United States Patent
Schwarze et al.

(10) Patent No.: US 7,871,047 B2
(45) Date of Patent: Jan. 18, 2011

(54) FIXTURE FOR SPATIAL POSITIONING OF A DEVICE

(75) Inventors: Werner Schwarze, Jena (DE); Hugo Stephan, Jena (DE); Andreas Martin, Jena (DE)

(73) Assignee: AST GmbH, Jena (DE)

( * ) Notice: Subject to any disclaimer, the term of this patent is extended or adjusted under 35 U.S.C. 154(b) by 352 days.

(21) Appl. No.: 11/924,398

(22) Filed: Oct. 25, 2007

(65) Prior Publication Data
US 2009/0014607 A1 Jan. 15, 2009

(30) Foreign Application Priority Data
Oct. 27, 2006 (DE) .................. 10 2006 050 781

(51) Int. Cl.
*F16M 11/00* (2006.01)
(52) U.S. Cl. .................. 248/176.1; 248/278.1
(58) Field of Classification Search .............. 248/176.1, 248/274.1, 278.1; 384/445
See application file for complete search history.

(56) References Cited

U.S. PATENT DOCUMENTS

| 4,276,779 | A |   | 7/1981 | Davis, Jr. et al. |
|---|---|---|---|---|
| 4,537,074 | A |   | 8/1985 | Dietz et al. |
| 4,539,989 | A |   | 9/1985 | Forssmann et al. |
| 4,807,627 | A |   | 2/1989 | Eisenmenger |
| 4,984,575 | A |   | 1/1991 | Uchiyama et al. |
| 5,119,801 | A |   | 6/1992 | Eisenhoefer et al. |
| 5,174,280 | A |   | 12/1992 | Gruenwald et al. |
| 5,222,484 | A |   | 6/1993 | Krauss et al. |
| 5,287,856 | A |   | 2/1994 | Treiber |
| 5,301,660 | A |   | 4/1994 | Rattner |
| 5,350,351 | A |   | 9/1994 | Saffer |
| 5,419,327 | A |   | 5/1995 | Rohwedder et al. |
| 5,419,335 | A |   | 5/1995 | Hartmann et al. |
| 5,451,010 | A | * | 9/1995 | Heuser ............... 242/530.3 |
| 5,545,124 | A |   | 8/1996 | Krause et al. |
| 5,595,178 | A |   | 1/1997 | Voss et al. |
| 5,921,930 | A |   | 7/1999 | Uberle |
| 6,128,575 | A |   | 10/2000 | Croom et al. |
| 6,306,089 | B1 |   | 10/2001 | Coleman et al. |
| 6,434,216 | B1 | * | 8/2002 | Maki et al. ............... 378/9 |
| 6,695,270 | B1 | * | 2/2004 | Smed ............... 248/274.1 |
| 7,207,714 | B1 | * | 4/2007 | Dhillon ............... 378/204 |
| 2001/0023326 | A1 |   | 9/2001 | Spector |
| 2001/0039379 | A1 |   | 11/2001 | Hagelauer |

(Continued)

FOREIGN PATENT DOCUMENTS

DE  3427001  1/1986

(Continued)

*Primary Examiner*—Ramon O Ramirez
(74) *Attorney, Agent, or Firm*—King & Spalding LLP

(57) ABSTRACT

In a fixture for spatial positioning of a device, in particular a device for a medical application, that is supported in a pivoting arrangement on a holding device or the like by means of an arm, quick and easy alignment of the device in relation to a person's treatment area is provided. This alignment is achieved in that a ring-shaped holding body is attached to the free end of the arm, that a spherical outer jacket surface is provided on the device with the surface enclosed wholly or in part by the holding body, and that the outer jacket surface of the device is held in the holding body and can be pivoted relative to the holding body.

31 Claims, 4 Drawing Sheets

U.S. PATENT DOCUMENTS

| | | |
|---|---|---|
| 2003/0174809 A1 | 9/2003 | Neumann |
| 2005/0010140 A1 | 1/2005 | Forssmann |
| 2008/0033287 A1 | 2/2008 | Schwarze et al. |
| 2009/0216160 A1 | 8/2009 | Schwarze |

FOREIGN PATENT DOCUMENTS

| | | | |
|---|---|---|---|
| DE | 4039408 | 6/1991 | |
| DE | 10065450 | 7/2002 | |
| DE | 102005017724 | 11/2006 | |
| EP | 1445758 | 8/2004 | |
| FR | 2690719 A1 * | 11/1993 | ................. 384/428 |
| WO | WO 2006/010865 | 10/2006 | |
| WO | WO 2006/108615 | 10/2006 | |

* cited by examiner

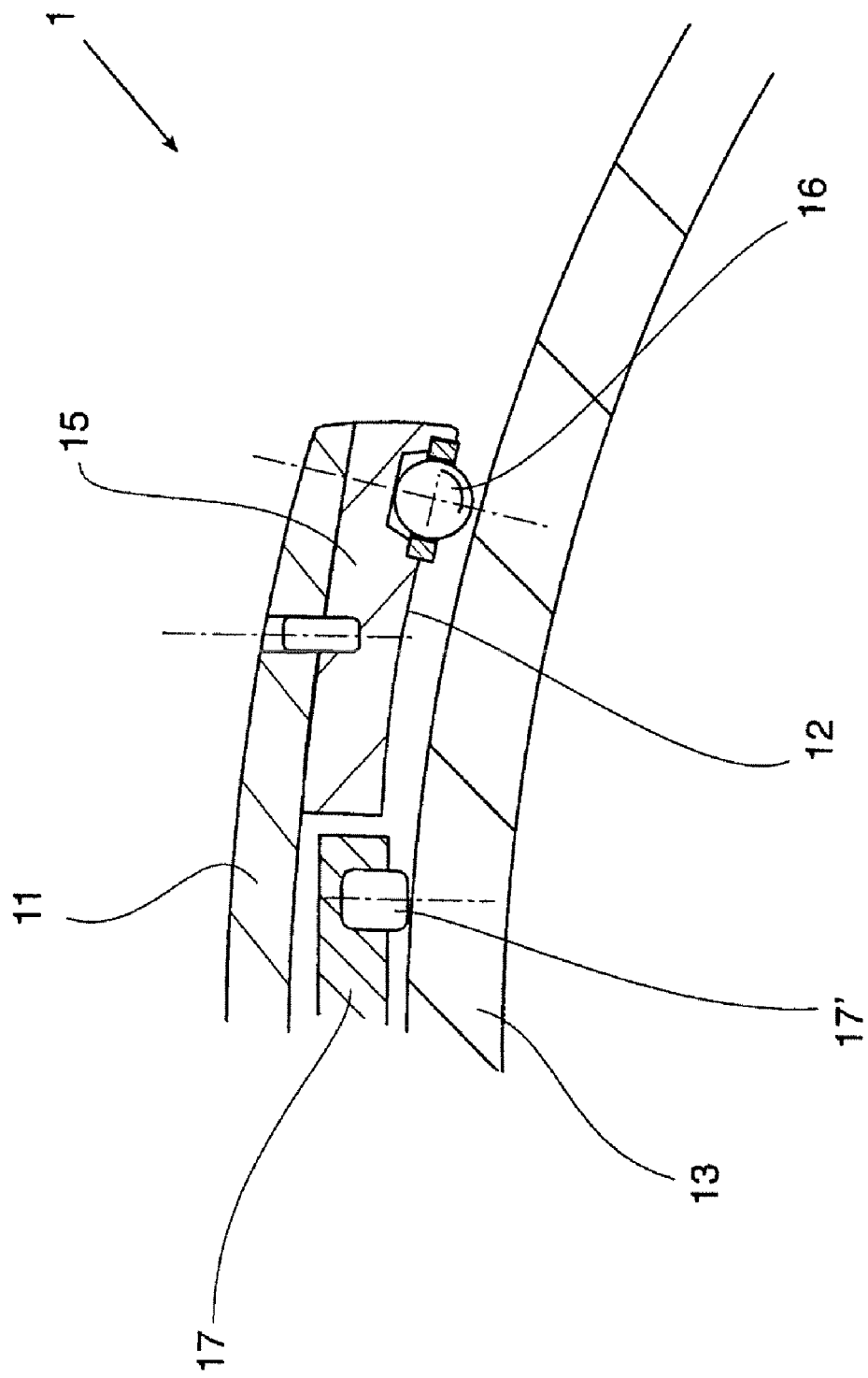

FIXTURE FOR SPATIAL POSITIONING OF A DEVICE

RELATED PATENT APPLICATIONS

This patent application claims priority to German Patent Application No. 10 2006 050 781.9 filed Oct. 27, 2006. The complete disclosure of the above-identified patent application is hereby fully-incorporated herein by reference.

TECHNICAL FIELD

The present invention relates to a fixture for spatial positioning of a device. More particularly, the invention relates to a fixture for spatial positioning of a device with a medical application, that is supported in a pivoting arrangement on a holding device or the like by an arm.

BACKGROUND

Devices for positioning a medical device generally require the treatment area to be positioned centrally in relation to the holding fixture. In such conventional methods, the positioning fixture can be moved in space along a rail bent into a C-shape. The patient's treatment area is preferably positioned in the center of the C-shaped rail. A fixture of this kind can be used for supporting both X-ray and shock wave generation devices for treating bone growth or for lithotripsy of kidney stones. Accordingly, the medical device is aligned along an arc located on the same plane as the patient's treatment area.

A disadvantage of the conventional devices is that the treatment area must be positioned centrally in relation to the arc-shaped arrangement of the holding fixture in order for the X-ray beams or the focal point of the generated shock waves to be oriented specifically for the device. Thus, even minor positioning inaccuracies outside the center point of the holding fixture can lead to unwanted medical side effects. For example, the shock waves can have a characteristic that is not suitable for the required successful treatment effect in this position. Therefore, it is necessary to ensure at all times that the patient's treatment area is positioned precisely in the spatial area of the center of the arc-shaped holding fixture.

A further disadvantage of conventional methods is that the device can only be aligned in one plane in relation to the treatment area. As a result, geometrical adaptations intended to arrange the treatment area in the specified center point are very time consuming because the treatment area, i.e. the patient, must be precisely positioned with regard to the holding fixture and must be fixed in this position for the duration of the treatment. This is because the device in accordance with the prior art can only be used along the holding fixture in accordance with the rail bent into a C-shape, meaning that the alignment of the device is two-dimensional.

Thus, a need exists in the art for a device that addresses the deficiencies of conventional devices.

SUMMARY

The present invention can provide a fixture for spatial positioning of a device such that the device can be aligned and secured in space in relation to a patient's treatment area, with the movement of the device being easy and efficient.

In one aspect of the invention, a ring-shaped holding body is attached to the free end of an arm, and a spherical outer jacket surface is provided on the device. The spherical outer jacket surface is enclosed in whole or in part by the ring-shaped holding body. The outer jacket surface of the device is held in the holding body and can be swiveled relative to the holding body.

The inside of the holding body can be arranged at a distance from the outer jacket surface, such that the inside of the holding body runs concentrically to the outer jacket surface. Further, at least one plain and/or antifriction bearing can be arranged between the holding body and the outer jacket surface, supported against the holding body and acting against the outer jacket surface. The plain and/or anti-friction bearings permit a relative movement between the device and the holding body as a component of the holding fixture, and this relative movement can be performed in two of the three spatial vectors.

In one aspect of the invention, the plain and/or anti-friction bearings can comprise two rings coupled to the inside of the holding body and aligned such that a space does not exist between the two rings. Further, the two rings can be parallel to one another and perpendicular to the lengthwise axis of the device. The plain and/or anti-friction bearings can comprise spherical roller bodies arranged in the two rings and can vertically contact the spherical outer jacket surface of the device. In addition, the two rings can be disposed in the ends of the holding body, and the curvature of the two rings can run concentrically with the spherical outer jacket surface. The spherical outer jacket surface can have a surface that provides for as little friction as possible to allow the roller bodies to move easily along it.

The movement between the outer jacket surface and the holding body is guaranteed by the geometrical arrangement of the outer jacket surface and the inner contour of the holding body that is adapted to the outer jacket surface, without the device slipping out of the holding body as a result of the positioning possibilities. Instead, the ring-shaped holding body partially or entirely encloses the outer jacket surface in order to support it and, at the same time, to provide a relative movement in space.

The alignment and positioning options of the device in the space are increased because the holding device is arranged on an arm with a swivel joint provided at its end between the end of the arm and the holding body. Thus, the device can be swiveled about the lengthways axis of the arm. As a result, two subsections overlap allowing for adjustment of the device in a vertical plane. Both subsections of the adjusting angle overlap within a spatially limited area in order to achieve an overall adjusting angle range of +/−45 degrees. Furthermore, the device can be moved within an adjusting angle of +/−26 degrees in an adjusting plane running perpendicular to the lengthways axis of the device and parallel to the lengthways axis of the arm so that the overlapping of the two adjusting movements allows the device to be aligned diagonally in space overall. In this regard, the total adjustment available is +/−71 degrees (the total of the 26 degree and 45 degree subsections) with respect to the horizontal axis of the device.

The adjusting angle is limited by the geometrical dimensions of the outer jacket surface with regard to the diameter of the cylindrically shaped device. The cylindrical jacket surface of the device arranged immediately adjacent to the outer jacket surface namely acts as a stop and is in contact with the side area of the holding body at the maximum possible set deflection.

According to one aspect, two guide elements can be provided on the swivel joint. The two guide elements can be arranged with one inside the other in the form of a dovetail guide. This arrangement can provide for rotation of the device. Openings in the dovetail guide can be closed by a cover that is aligned along the lengthwise axis of the arm.

Further, a brake can be disposed in the central plane of the holding body, such that it contacts the spherical outer jacket such that activation of the brake can stop the movement of the device. The brake can comprise a two-part ring, where an actuator can press the two-part ring apart, allowing movement of the device; and a spring can press the two-part ring together, essentially preventing movement of the device.

Additional aspects of the invention include supports struts on the arm that can be telescoped inside one another, and one or more handles on the device to facilitate movement.

BRIEF DESCRIPTION OF THE DRAWINGS

The drawings show sample embodiments in accordance with the present invention, the details of which are explained hereinafter.

FIG. 4 shows a magnified partial view of the fixture from FIG. 2 in the area IV.

DETAILED DESCRIPTION OF EXEMPLARY EMBODIMENTS

Figure 1:
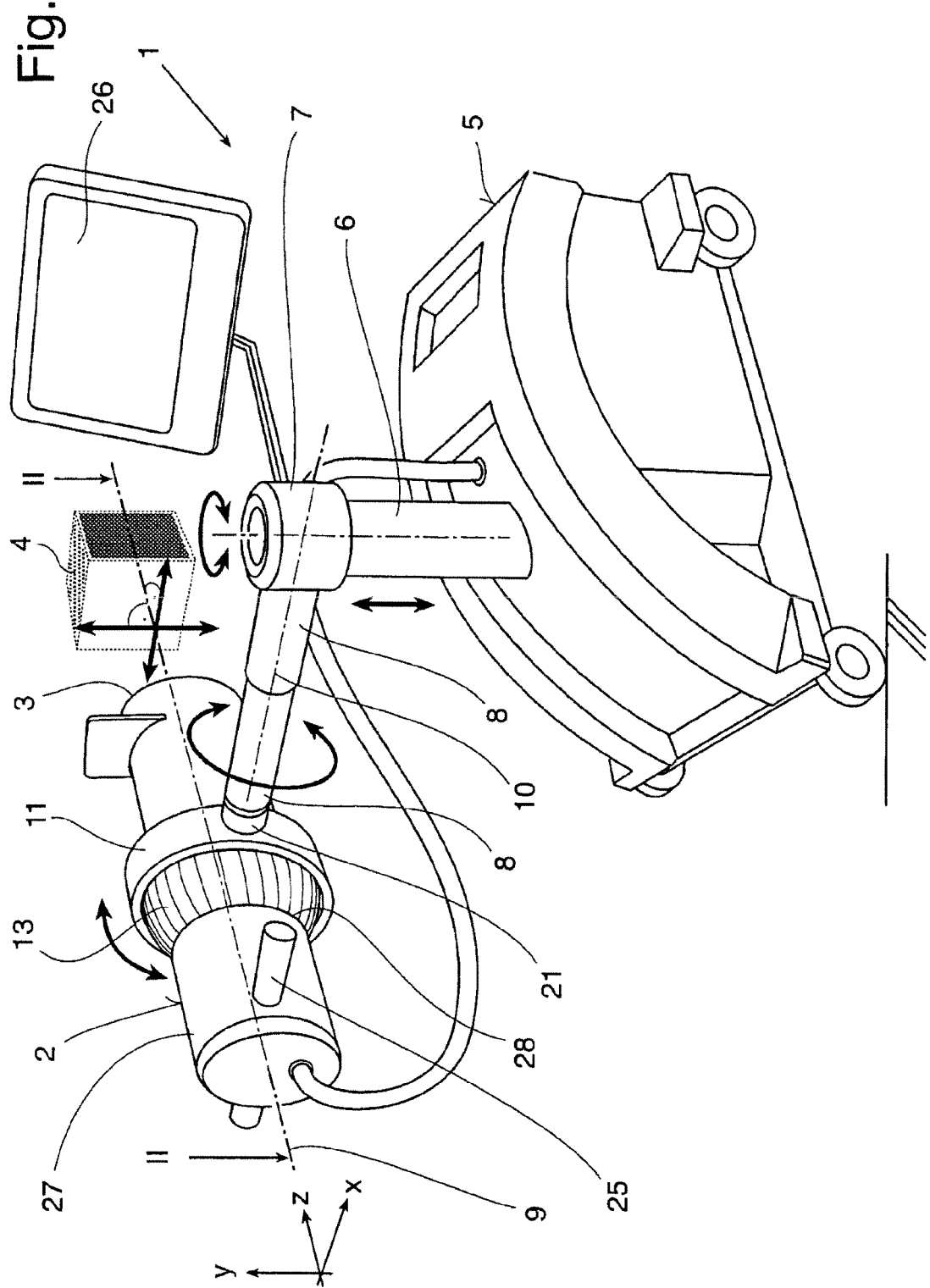
FIG. 1 shows a fixture for spatial positioning of a shock wave generator device that is supported by an arm on a holding device, in a perspective view.

Referring to the drawings, in which like numerals represent like elements, aspects of the exemplary embodiments will be described.

FIG. 1 shows a fixture 1 for holding a medical device 2 by means of which, for example, shock waves can be generated for lithotripsy of kidney stones or for treating bone growth or for healing wounds. The shock waves generated by the device 2 pass through a diaphragm bellows 3 into a treatment area 4. Treatment area 4 is indicated schematically and located inside a patient (not illustrated). The diaphragm bellows 3 contacts the patient's skin or is arranged at a distance from the patient. The medical device 2 can also be configured as an X-ray device or the like and be arranged at a distance from the treatment area 4 or the patient.

The device 2 is attached to a holding device 5 configured as a carriage by means of an L-shaped arm 6. The holding device 5 can be moved along a base. The L-shaped arm 6 consists of a swivel joint 7 arranged between the sections of the arm 6 such that the arm 6 can be pivoted through 360 degrees in relation to the holding device 5. Furthermore, the swivel joint 7 can be moved along with the vertical section of the arm 6 in order to adjust the height.

A swivel joint 21 is disposed at the free end of the arm 6 and is explained in more detail below. A holding body 11 is attached to the swivel joint 21, and the entirety of the holding body 11 forms a completely enclosed ring. The holding body 11 is configured in two parts for installation and removal purposes. Furthermore, the holding body 11 can be configured as an open ring with a ring section of at least 185 degrees.

The device 2 consists of a housing with a cylinder-shaped jacket surface 27. A spherical outer jacket surface 13 is provided approximately in the geometrical center of the device 2 and is completely or partly enclosed by the holding body 11. The device 2 is thus supported by the holding device 5 by the holding body 11 in such a way that the device 2 can be moved relative to the holding body 11.

Figure 2:
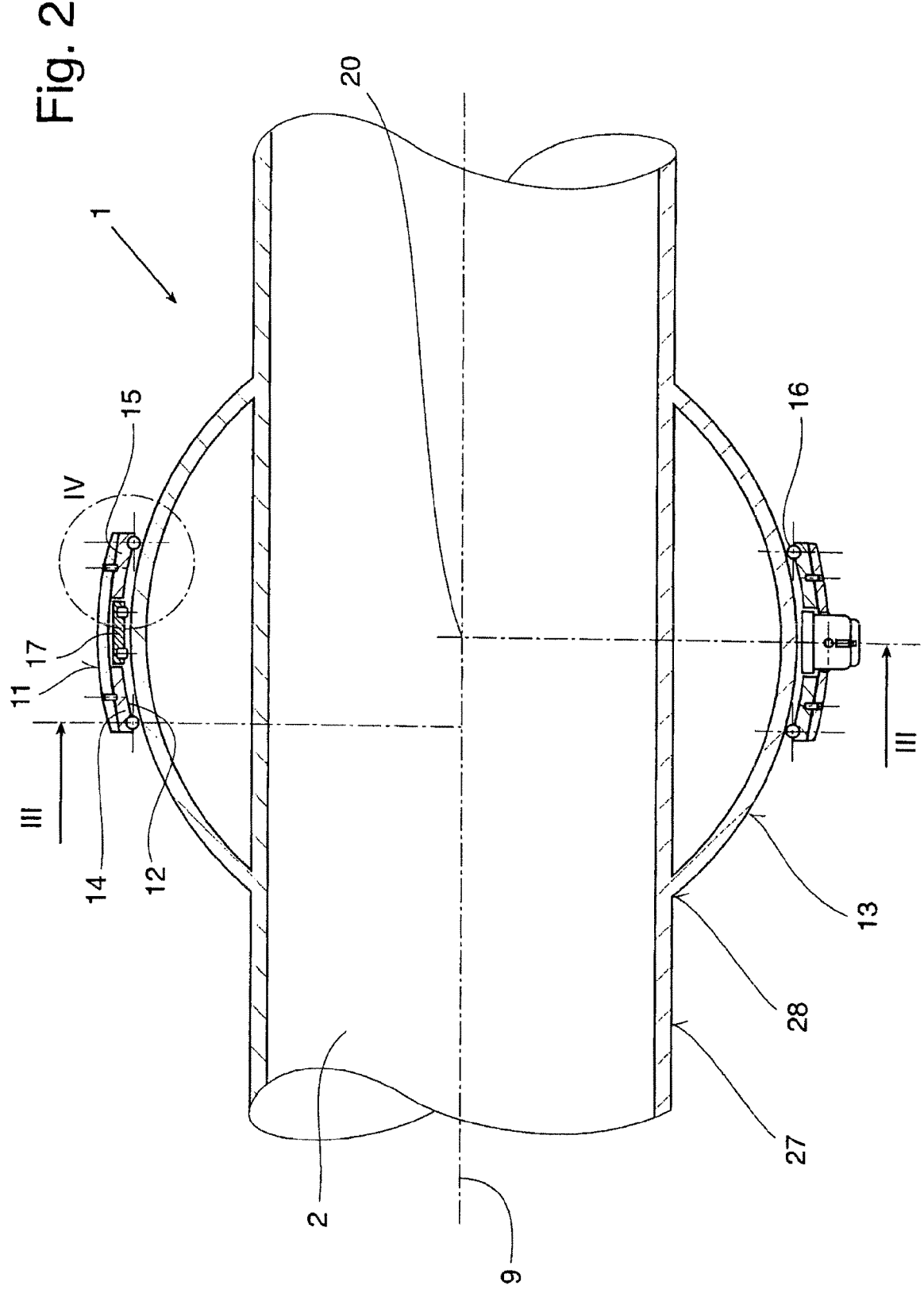
FIG. 2 shows the fixture in accordance with FIG. 1, along the section line II-II.

FIGS. 2 and 4 show that the holding body 11 has a concentrically curved inside 12 that runs at a distance from the outer jacket surface 13. There should be a constant distance between these two surfaces 12 and 13 in order to accommodate a plain or anti-friction bearing by means of which the device 2 is supported in a pivoting arrangement on the holding body 11. Two rings 14, 15 are inserted on the inside 12 of the holding body 11. A plurality of balls 16 is inserted in these rings 14, 15 in a rotating arrangement. The rings 14, 15 therefore combine with the balls 16 to form two anti-friction bearings located at a distance from one another by means of which the outer jacket surface 13 is held in a pivoting arrangement without the possibility of the device 2 being pulled out from the holding body 11 in the direction of its lengthways axis 9. In an alternative embodiment, one or two plain bearings can be accommodated in the inside of the holding body 11. The lengthways axis 9 in this case corresponds to the Z-axis of the system of coordinates shown in FIG. 1. The range of movement of the device 2 or the diaphragm bellows 3 is defined by the plane formed by the X-axis and the Y-axis.

The distance between the inside 12 and the outer jacket surface 13 corresponds to the spherical radius of the balls 16. Furthermore, the balls 16 make perpendicular contact with the outer jacket surface 13 irrespective of the angle position of the outer jacket surface 13 in relation to the holding body 11. Furthermore, a brake 17 is arranged on the inside 12 of the holding body 11, and the brake 17 is held in a fixed location in the holding body 11 and runs approximately centrally between the two rings 14, 15. The brake 17 acts on the outer jacket surface 13 in such a way that the movement of the device 2 is stopped by brake bodies 17' (FIG. 4) inserted in the brake 17. For this purpose, the brake 17 is composed of two holding rings, the free opposite ends of which are held together by an actuator 18.

Figure 3:
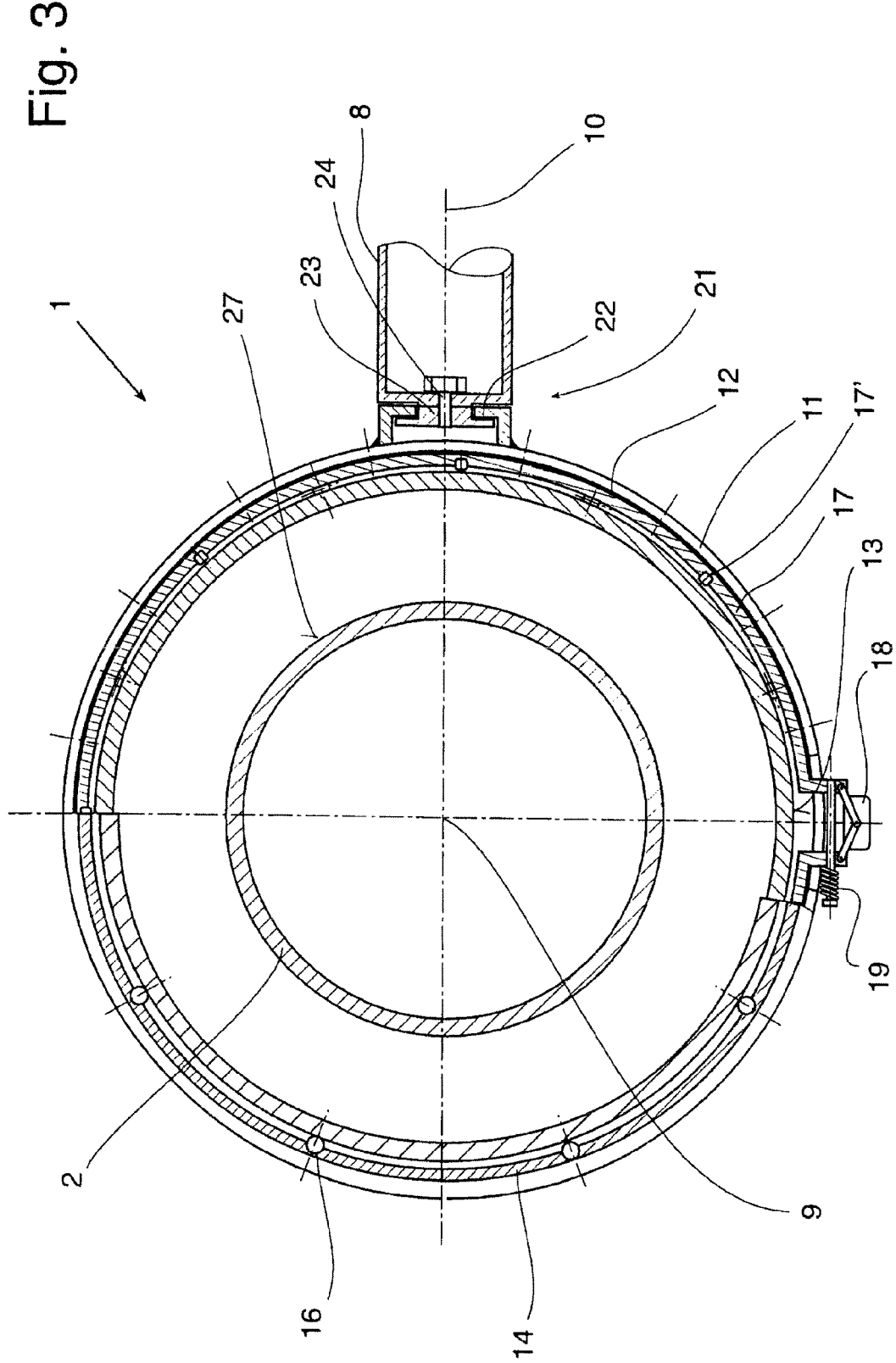
FIG. 3 shows the fixture in accordance with FIG. 2, along the section line III-III.

FIG. 3 shows the actuator 18 that is connected to the two free ends of the brake 17 by means of an angle lever 18'. Moving the actuator 18 towards the device 2 therefore presses apart the two free ends due to the effect of the angle lever, and consequently the internal diameter of the brake 17 increases such that the friction force acting on the outer jacket surface 13 is reduced or entirely cancelled. The brake bodies 17' are—arranged at a distance from the outer jacket surface 13. Thus, the device 2 can be moved relative to the holding body 11. In addition, movement of the actuator 18 presses a return spring 19 together. If the actuator 18 is then released, the return spring 19 presses the two free ends of the brake 17 together with the effect that braking force once again acts on the outer jacket surface 13 by means of the brake bodies 17'. Thus, movement of the device 2 relative to the holding body 11 is not possible, or only possible by exerting considerable force.

Furthermore, FIG. 3 shows that the holding body 11 is connected by the swivel joint 21. The swivel joint 21 is configured in the form of a dovetail guide 22. One section of the arm 6 is composed of two struts 8 that can be pushed one inside the other in a telescopic arrangement. For installation purposes, the struts 8 can be disconnected from one another with the effect that the inside of the subsection assigned to the holding body 11 can be accessed from the outside. A cover 23 is provided for covering the dovetail guide 22, with the cover 23 being locked in place by a screw 24 arranged inside the strut 8. Thus, the holding body 11 can be moved perpendicularly about the lengthwise axis of the strut 8 due to the presence of the swivel joint 21. FIG. 1 in particular shows the directions in which the device 2 can be aligned in space. Two handles 25 are provided on opposite sides of the device 2 for this purpose.

The device 2 can be moved in a vertical direction about the swivel joint 21, i.e., about the lengthwise axis of the struts 8.

Furthermore, the device 2 can be aligned in a plane running parallel to the lengthways axis of the struts 8 because the outer jacket surface 13 can be moved within the holding body 11 until the cylinder jacket surface 27 that runs in the area of the outer jacket surface 13 makes contact with the end of the holding body 11 as a stop 28. In the selected sample embodiment, the geometrical relationships between the diameter of the outer jacket surface 13 and the internal diameter of the holding body 11 have been selected in such a way that an adjustment angle a of +/−26 degrees about the center 20 of the device 2 is possible. This is a first subsection of the adjustment angle a. A second subsection of the adjustment angle a is generated by means of the opportunities to rotate the swivel joint 21. The deflection in a vertical direction, i.e. in the plane running at right angles to the lengthways axis 9 of the device 2, is approx. +/−45 degrees." In this regard, the total adjustment available is +/−71 degrees (the total of the 26 degree and 45 degree subsections) with respect to the horizontal axis of the device.

Due to the design of the fixture 1, it is now possible for the patient and/or his or her treatment area 4 to remain fixed and stationary. The device 2 can be positioned precisely in relation to the treatment area 4 without the need for the area to be moved. A monitor 26 with a localization and navigation system (not illustrated) is provided for this purpose, by means of which a doctor conducting the treatment is able to monitor continuously the alignment of the device 2 in relation to the treatment area 4.

The invention claimed is:

1. A system for spatial positioning of a medical device that is supported in a pivoting arrangement on a holding device, the system comprising:
   an arm comprising a free end;
   a holding body coupled to the free end of the arm, the holding body being at least partially ring-shaped;
   a spherical outer jacket surface coupled to the device; and
   a brake disposed on an inside of the holding body such that the brake contacts the spherical outer jacket surface, wherein the brake is operable external to the holding body and has a holding effect on the spherical outer jacket surface,
   wherein the surface of the spherical outer jacket is enclosed at least in part by the holding body and held in the holding body, and
   wherein the spherical outer jacket is movable and can be swiveled relative to the holding body.

2. The system of claim 1, wherein an inside surface of the holding body is arranged at a distance from the spherical outer jacket surface, such that the inside surface of the holding body and the spherical outer jacket surface are disposed concentrically with one another.

3. The system of claim 2, wherein at least one bearing is disposed between the holding body and the spherical outer jacket surface, the at least one bearing being supported against the holding body and acting against the spherical outer jacket surface.

4. The system of claim 3, wherein the at least one bearing comprises:
   two rings coupled to the inside of the holding body and aligned such that a space exists between the two rings, the two rings being disposed parallel to one another and perpendicular to the lengthwise axis of the device; and
   a plurality of roller bodies disposed in the two rings, the plurality of roller bodies projecting from the two rings, contacting the spherical outer jacket surface of the device, and mounted in a rotating arrangement in the two rings.

5. The system of claim 4, wherein the roller bodies comprise a spherical shape.

6. The system of claim 4, wherein the two rings are disposed near ends of the holding body, and
   wherein the curvature of the two rings runs concentrically with the spherical outer jacket surface.

7. The system of claim 4, wherein the roller bodies contact the spherical outer jacket surface of the device vertically.

8. The system of claim 4, wherein the spherical outer jacket surface is configured to allow the roller bodies to roll along the spherical outer jacket surface with a minimal amount of friction.

9. The system of claim 1, further comprising a swivel joint disposed between the holding body and the arm, such that the device is movable along an axis perpendicular to a lengthwise axis of the arm.

10. The system of claim 9, wherein the swivel joint comprises two guide elements disposed one inside the other in a rotatable arrangement.

11. The system of claim 10, wherein the two guide elements are coupled together in the form of a dovetail guide, the dovetail guide comprising a plurality of openings.

12. The system of claim 11, wherein the plurality of openings in the dovetail guide is closed by a cover, the cover aligned along the lengthwise axis of the arm.

13. The system of claim 1, wherein the brake comprises:
   a two-part ring that surrounds at least a portion of the spherical outer jacket surface; and
   an actuator that presses ends of the two-part ring apart when activated; and
   a spring that presses the ends of the two-part ring together.

14. The system of claim 1, wherein the brake is disposed in a central plane of the holding body.

15. The system of claim 1, wherein the arm comprises two support struts telescopically arranged such that one of the struts can move inside the other one of the struts.

16. The system of claim 1, further comprising at least one apparatus coupled to the device such that an open operation of the apparatus moves the device.

17. The system of claim 1, wherein a surface of the device runs parallel to a lengthwise axis of the device in an area of the spherical outer jacket surface and limits freedom of movement of the device.

18. The system of claim 1, wherein the device is movable in a first plane and a second plane.

19. The system of claim 18, wherein the first plane runs perpendicular to a lengthwise axis of the device and has an adjusting angle ranging from −26 degrees to +26 degrees.

20. The system of claim 18, wherein the second plane runs perpendicular to the first plane and has an adjusting angle ranging from −45 degrees to +45 degrees, and
   wherein the adjusting angle is divided into two different adjustment sections.

21. The system of claim 1, further comprising at least one handle coupled to the device such that movement of the handles moves the device.

22. A system for spatial positioning of a medical device that is supported in a pivoting arrangement on a holding device, the system comprising:
   an arm comprising a free end;
   a holding body coupled to the free end of the arm, the holding body being at least partially ring-shaped; and
   a spherical outer jacket surface coupled to the device,
   wherein the surface of the spherical outer jacket is enclosed at least in part by the holding body and held in the holding body, and an inside surface of the holding body is arranged at a distance from the spherical outer jacket surface, such that the inside surface of the holding body and the spherical outer jacket surface are disposed concentrically with one another, wherein the spherical outer jacket is movable and can be swiveled relative to the holding body, and wherein at least one bearing is disposed between the holding body and the spherical outer jacket surface, the at least one bearing being supported against the holding body and acting against the spherical outer jacket surface, the at least one bearing comprising:

two rings coupled to the inside of the holding body and aligned such that a space exists between the two rings, the two rings being disposed parallel to one another and perpendicular to the lengthwise axis of the device; and a plurality of roller bodies disposed in the two rings, the plurality of roller bodies projecting from the two rings, contacting the spherical outer jacket surface of the device, and mounted in a rotating arrangement in the two rings.

23. The system of claim 2, wherein the roller bodies comprise a spherical shape.

24. The system of claim 22, wherein the two rings are disposed near ends of the holding body, and wherein the curvature of the two rings runs concentrically with the spherical outer jacket surface.

25. The system of claim 22, wherein the roller bodies contact the spherical outer jacket surface of the device vertically.

26. The system of claim 22, wherein the spherical outer jacket surface is configured to allow the roller bodies to roll along the spherical outer jacket surface with a minimal amount of friction.

27. A system for spatial positioning of a medical device that is supported in a pivoting arrangement on a holding device, the system comprising:

an arm comprising a free end;

a holding body coupled to the free end of the arm, the holding body being at least partially ring-shaped;

a spherical outer jacket surface coupled to the device; and a swivel joint disposed between the holding body and the arm such that the device is movable along an axis perpendicular to a lengthwise axis of the arm, wherein the surface of the spherical outer jacket is enclosed at least in part by the holding body and held in the holding body, wherein the spherical outer jacket is movable and can be swiveled relative to the holding body.

28. The system of claim 27, wherein the swivel joint comprises two guide elements disposed one inside the other in a rotatable arrangement.

29. The system of claim 28, wherein the two guide elements are coupled together in the form of a dovetail guide, the dovetail guide comprising a plurality of openings.

30. The system of claim 29, wherein the plurality of openings in the dovetail guide is closed by a cover, the cover aligned along the lengthwise axis of the arm.

31. A system for spatial positioning of a medical device that is supported in a pivoting arrangement on a holding device, the system comprising:

an arm comprising a free end;

a holding body coupled to the free end of the arm, the holding body being at least partially ring-shaped; and a spherical outer jacket surface coupled to the device, wherein the surface of the spherical outer jacket is enclosed at least in part by the holding body and held in the holding body, wherein the spherical outer jacket is movable and can be swiveled relative to the holding body, and wherein the device is movable in a first plane and a second plane, the second plane running perpendicular to the first plane and having an adjusting angle ranging from −45 degrees to +45 degrees, the adjusting angle divided into two different adjustment sections.

* * * * *